(12) United States Patent
Quay

(10) Patent No.: US 9,295,658 B2
(45) Date of Patent: Mar. 29, 2016

(54) SECOND GENERATION FATTY ACID COMPOSITIONS, FORMULATIONS, AND METHODS OF USE AND SYNTHESIS THEREOF

(71) Applicant: DRACOPHARMA, INC., Seattle, WA (US)

(72) Inventor: Steven C. Quay, Seattle, WA (US)

(*) Notice: Subject to any disclaimer, the term of this patent is extended or adjusted under 35 U.S.C. 154(b) by 0 days.

(21) Appl. No.: 14/215,395

(22) Filed: Mar. 17, 2014

(65) Prior Publication Data

US 2014/0200267 A1 Jul. 17, 2014

Related U.S. Application Data

(60) Continuation of application No. 13/761,243, filed on Feb. 7, 2013, now abandoned, which is a division of application No. 12/852,620, filed on Aug. 9, 2010, now abandoned.

(60) Provisional application No. 61/288,587, filed on Dec. 21, 2009, provisional application No. 61/232,554, filed on Aug. 10, 2009.

(51) Int. Cl.
| | |
|---|---|
| *A61K 31/16* | (2006.01) |
| *A61K 31/353* | (2006.01) |
| *A23L 1/30* | (2006.01) |
| *A61K 9/14* | (2006.01) |
| *A61K 9/48* | (2006.01) |
| *A61K 31/355* | (2006.01) |
| *A61K 31/164* | (2006.01) |

(52) U.S. Cl.
CPC .............. *A61K 31/16* (2013.01); *A23L 1/3008* (2013.01); *A61K 9/145* (2013.01); *A61K 9/146* (2013.01); *A61K 9/4858* (2013.01); *A61K 9/4866* (2013.01); *A61K 31/164* (2013.01); *A61K 31/353* (2013.01); *A61K 31/355* (2013.01)

(58) Field of Classification Search
CPC ...... A23L 1/3008; A61K 9/145; A61K 9/146; A61K 9/4858; A61K 31/355; A61K 31/164
USPC .................................................. 424/456, 94
See application file for complete search history.

*Primary Examiner* — Johann R Richter
*Assistant Examiner* — Yanzhi Zhang
(74) *Attorney, Agent, or Firm* — Andrew S. Langsam; Pryor Cashman LLP

(57) ABSTRACT

An orally administered fatty acid composition for the treatment of cardiovascular diseases, and a method of treating same, are provided. The compound includes 5Z,8Z,11Z,14Z,17Z-eicosapentaenoic ethanolamide (EPA ethanolamide), 4Z,7Z,10Z,13Z,16Z,19Z-docosahexaenoic ethanolamide (DHA ethanolamide), and at least one tocotrienol. The EPA ethanolamide and the DHA ethanolamide are preferably each substantially in a range of 100-900 mg per dosage form. The at least one tocotrienol is substantially in a range of 10-500 mg per dosage form. The at least one tocotrienol includes at least one of α-tocotrienol, β-tocotrienol, γ-tocotrienol, or δ-tocotrienol and is preferably substantially tocopherol-free. The composition may take the form of a medical food or a pharmaceutical preparation. A preferred formulation of the composition includes approximately 525 mg EPA ethanolamide, approximately 315 mg DHA ethanolamide, and approximately 50 mg δ-tocotrienol. The EPA and DHA ethanolamides may be synthesized from fatty acid triglycerides.

9 Claims, No Drawings

SECOND GENERATION FATTY ACID COMPOSITIONS, FORMULATIONS, AND METHODS OF USE AND SYNTHESIS THEREOF

RELATED APPLICATIONS

This Application is a Continuation Application of, and claims priority to, U.S. Non-Provisional application Ser. No. 13/761,243, filed Feb. 7, 2013, which itself is a Divisional Application of U.S. Non-Provisional application Ser. No. 12/852,620, filed Aug. 9, 2010, which itself claims priority to U.S. Provisional Patent Application No. 61/232,554 entitled "Second Generation Fatty Acid Compositions, Formulations, and Methods of Use and Synthesis Thereof," filed Aug. 10, 2009, and U.S. Provisional Patent Application 61/288,587 entitled "Second Generation Fatty Acid Compositions, Formulations, and Methods of Use and Synthesis Thereof," filed Dec. 21, 2009, the entireties of all of which are incorporated herein by reference.

BACKGROUND OF THE INVENTION

1. Field of the Invention

The present invention relates to a method utilizing a single administration or a unit dosage of omega-3 fatty acids and/or omega-3 fatty acid amides for the treatment of patients with dyslipidemias, including hypertriglyceridemia, high LDL-C serum levels, coronary heart disease (CHD), vascular disease, artherosclerotic disease, hypertension, and related conditions, and the prevention or reduction of cardiovascular and vascular events.

2. Description of Related Art

Cardiovascular diseases leading to morbidity and premature mortality are related to several risk factors such as hypertension, hypertriglyceridemia, hypercholesterolemia, high blood platelet aggregation and according to recent findings, a high activity of the blood coagulation factor VII phospholipid complex. Over the last four decades, antihypertensive drugs have contributed to the decline in cardiovascular disease-related morbidity and mortality. There is, however, heightened concern about side effects and toxicity associated with the current antihypertensive therapy, especially in the mildly hypertensive patient. There are results indicating that, although some antihypertensive agents are efficient in reducing blood pressure, the pulse rate is coincidentally increased. Thus, there is a need for a drug with fewer adverse effects for the treatment of hypertension. It would be particularly advantageous if such a drug could be used for the simultaneous treatment of all the above mentioned multiple risk factors associated with cardiovascular diseases, which is generally not the case with the currently available antihypertensive drugs.

During the late 1980s through the mid-1990s, numerous publications appeared which report that various dietary fish oil preparations containing omega-3 polyunsaturated fatty acids have the effect of lowering serum triglycerides and cholesterol.

There are currently over 40 different non-prescription, over-the-counter products containing omega-3 fatty acids, usually as triglycerides. In these formulations, the triglycerides are polydisperse, containing both saturated as well as unsaturated fatty acids. For example, flax seed oil has a typical composition as follows:

| Oil or Fat | Unsat./Sat. ratio | Saturated | | | | | Mono unsaturated | Poly unsaturated | |
|---|---|---|---|---|---|---|---|---|---|
| | | Capric Acid C10:0 | Lauric Acid C12:0 | Myristic Acid C14:0 | Palmitic Acid C16:0 | Stearic Acid C18:0 | Oleic Acid C18:1 | Linoleic Acid (ω6) C18:2 | Alpha Linolenic Acid (ω3) C18:3 |
| Flaxseed Oil | 9.0 | — | — | — | 3 | 7 | 21 | 16 | 53 |

In some cases the saturated fatty acids can interfere with the effects of the polyunsaturated omega-3 fatty acids.

U.S. Pat. Nos. 5,502,077 and 5,656,667, both to Breivik et al., describe a lipid-regulating agent, as a liquid-filled gel capsule for oral administration. Each 1-gram capsule of this formulation, which is commercialized as Lovaza® (GSK, Research Triangle Park, N.C. 27709), contains at least 900 mg of the ethyl esters of omega-3 fatty acids. These are predominantly a combination of ethyl esters of eicosapentaenoic acid (EPA—approximately 465 mg) and docosahexaenoic acid (DHA—approximately 375 mg).

In patients with very high triglyceride levels (>500 mg/dL) Lovaza is reported to lower triglyceride levels 44.9% [Lovaza Package Insert, Table 2]. Unfortunately this formulation adversely affects low density lipoprotein cholesterol (LDL-C), increasing it by 44.5%. Patients are at an increased risk of cardiovascular diseases and events when their LDL-C increases.

There is therefore a need to provide the beneficial effects of omega 3-fatty acids in compositions and formulations that do not have the LDL-C raising effects of the prior art formulations but in fact lower both LDL-C and triglycerides.

SUMMARY OF THE INVENTION

It has been found that fatty acid compositions containing omega-3 fatty acid amides (rather than their ethyl esters), including the ethanolamine amides, in an acceptable formulation, not only lower abnormally high triglycerides but also cholesterol, in the form of LDL-C. Accordingly, a first aspect of the invention is a method of treating high triglyceride and high LDL-C blood levels in a mammalian patient. A therapeutically effective amount of omega-3 fatty acids and/or omega-3 fatty acid amides is administered in an acceptable carrier sufficient to lower both triglyceride and LDL-C blood levels. Preferably, the omega-3 fatty acids and/or omega-3 fatty acid amides include at least one of octadecatrienoic (ALA), eicosapentaenoic (EPA), or docosahexaenoic (DHA) acid or ethanolamide. More preferably, the composition includes both EPA and DHA. These compositions can also be formulated with other lipid-lowering compounds, including statins, niacin-containing compounds, cholesterol-absorbing blockers, ethanolamine, and/or an HMG-CoA reductase inhibitor, including one or more tocotrienols.

In another aspect of the invention, the invention includes a method of synthesizing omega-3 fatty acid ethanolamides from fatty acid triglycerides. While the synthesis of fatty acid ethanolamides from the ethyl esters of EPA and DHA derived from plant sources (flax seed) and mackerel pike (*Cololabis saira*) has been described, the synthesis from omega-3 fatty acid triglycerides has not been described.

In one aspect of the invention, an orally administered fatty acid composition includes 5Z,8Z,11Z,14Z,17Z-eicosapentaenoic ethanolamide (EPA ethanolamide), 4Z,7Z,10Z,13Z,16Z,19Z-docosahexaenoic ethanolamide (DHA ethanolamide); and at least one tocotrienol. The composition has a total aerobic plate count per g/mL of less than 20,000 cfu. Preferably, the EPA ethanolamide is substantially in a range of 100 mg to 900 mg per dosage form, the DHA ethanolamide is substantially in a range of 100 mg to 900 mg per dosage form, and the at least one tocotrienol is substantially in a range of 10 mg to 500 mg per dosage form.

The at least one tocotrienol includes at least one of α-tocotrienol, β-tocotrienol, γ-tocotrienol, or δ-tocotrienol and is preferably substantially tocopherol-free.

The composition may be a medical food, a pharmaceutical preparation, or another oral formulation.

Preferably, the orally administered fatty acid composition of the invention includes a capsule having approximately 525 mg EPA ethanolamide, approximately 315 mg DHA ethanolamide, and approximately 50 mg δ-tocotrienol. The capsule preferably has a gelatin base. Additionally, at least one of the EPA ethanolamide or the DHA ethanolamide may be synthesized from a respective fatty acid triglyceride.

In another aspect of the invention, a method of treating cardiovascular diseases includes the step of orally administering a therapeutically effective amount of a composition having 5Z,8Z,11Z,14Z,17Z-eicosapentaenoic ethanolamide (EPA ethanolamide), 4Z,7Z,10Z,13Z,16Z,19Z-docosahexaenoic ethanolamide (DHA ethanolamide), and at least one tocotrienol. Preferably, The EPA ethanolamide is substantially in a range of 100-900 mg per dosage form, the DHA ethanolamide is substantially in a range of 100-900 mg per dosage form, and the at least one tocotrienol is substantially in a range of 10-500 mg per dosage form. The at least one tocotrienol includes at least one of α-tocotrienol, β-tocotrienol, γ-tocotrienol, or δ-tocotrienol and is preferably substantially tocopherol-free. The orally administered composition may be a medical food, a pharmaceutical preparation, or other oral formulation.

Optionally, the composition comprises a capsule having approximately 525 mg EPA ethanolamide, approximately 315 mg DHA ethanolamide, and approximately 50 mg δ-tocotrienol. The EPA ethanolamide, the DHA ethanolamide, and the at least one tocotrienol may be provided in a capsule having a gelatin base. The method may optionally include the step of synthesizing at least one of the EPA ethanolamide or the DHA ethanolamide from a respective fatty acid triglyceride.

DEFINITIONS n-3 fatty acids (popularly referred to as ω-3 fatty acids or omega-3 fatty acids) are a family of unsaturated fatty acids that have in common a final carbon-carbon double bond in the n-3 position; that is, the third bond from the methyl end of the fatty acid.

This table lists several different names for the most common n-3 fatty acids found in nature.

TABLE I

| Common name | Lipid name | Chemical name |
| --- | --- | --- |
|  | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (STD) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-docosahexaenoic acid |
| Tetracosahexaenoic acid (Nisinic acid) | 24:6 (n-3) | all-cis-6,9,12,15,18,21-tetracosenoic acid |

DETAILED DESCRIPTION OF THE INVENTION

A more detailed description of the invention will now be given. It should be understood that this description is exemplary in nature and in no way serves to limit the scope of the invention, which is defined by the claims appearing hereinbelow.

The invention includes a preferably oral formulation (e.g., a pharmaceutical preparation or a medical food) of omega-3 fatty acid amides, including the ethanolamine amides. Unlike the ethyl esters or the triglycerides of omega-3 fatty acids, the amides have several beneficial effects without many of the concomitant negative effects. First, the amides of omega-3 fatty acids boost production of phospholipids by, among other reasons, contributing both the ethanolamine head group and the fatty acid chains to phosphatidylethanolamine and phosphatidylcholine. Second, they are metabolized into substances that are typically in short supply in the human body: ethanolamine and omega-3 fatty acids. Further, amides of omega-3 fatty acids should not raise LDL cholesterol levels as do the ethyl esters and triglycerides of omega-3 fatty acids. Indeed, in the preferred embodiment, when combined with one or more tocotrienols, omega-3 fatty acid amides should advantageously lower both triglycerides and LDL cholesterol. In the alternative to providing an oral formulation of the amides of omega-3 fatty acids, the invention also includes an oral formulation of omega-3 fatty acids and ethanolamine, preferably also including at least one tocotrienol.

Below are described exemplary and prophetic processes for synthesizing omega-3 fatty acid amides.

1. Lipid Extraction

Lipids can be extracted from flax seed and *saira* carcasses according to the literature method [E. G. Bligh and W. J. Dyer, *Can. J. Biochem. Physiol.*, 37, No. 8, 911 (1959).].

2. Synthesis of FA Ethanolamides from FA Ethyl Esters

The method of Karaulov et. al. (Synthesis of Fatty-Acid Ethanolamides from *Linum catharticum* Oils and *Cololabis saira* Fats, Chemistry of Natural Compounds, Vol. 40, No. 3, 2004), repeated here, can be used. In the reference, a mixture of FA ethyl esters (6.56 g) was treated with freshly distilled monoethanolamine (over KOH, 6.53 g, 1:5 mole ratio) and trifluoroacetic acid (10 μL). The mixture was sealed in an ampul, vigorously shaken, held for 2 h at 140° C., cooled to 25° C., and removed from the ampul. The contents were treated with $CHCl_3$ (10 mL) and aqueous HCl (10%) until the pH was 3. The resulting mixture was vigorously shaken. The $CHCl_3$ layer was separated after layering. The extraction was repeated twice. The $CHCl_3$ fractions were combined, dried over anhydrous $Na_2SO_4$, and evaporated in vacuum at 40° C. to constant mass. Yield 6.67 g (6.54 g for FA ethyl esters from flax-seed oil) as an opaque yellowish-orange oil containing 4.86 g (4.78 g for FA ethyl esters from flax-seed oil) of FA ethanolamides. The degree of conversion was about 70%. The purity of the FA ethanolamides was monitored by TLC. The FA ethanolamides were purified over a Chemapol L silica-gel column (Kavalier, Czech Rep., 40-100 μm) using a stepped gradient of acetone in hexane (0→10%) calculated as 2 g of starting ethanolamides per 60 g silica gel. Yield 900 mg of purified FA ethanolamides (Rf 0.47) from *saira* fat and flax-seed oil as colorless oily liquids for every 2 g of starting mixture placed on the column. An analogous procedure was performed using ethyl esters of α-linolenic, eicosapentaenoic, and docosahexaenoic acids to afford FA ethanolamides of these FA (Rf 0.47) as oily liquids in yields of 33, 34, and 35 mg, respectively, for each 100 mg of FA ethyl esters used in the reaction. All FA ethanolamides from pure FA ethyl esters and from mixtures were analyzed by HPLC-MS (APCI).

3. Prophetic Synthesis of FA Ethanolamides from FA Triglycerides

In accordance with the invention, FA ethanolamides can prophetically be synthesized directly from FA triglycerides, rather than from FA ethyl esters as described above. Specifically, the invention includes a method in which FA ethanolamides are to be prepared by aminolysis of the three ester bonds of the FA triglycerides by three mole equivalents of ethanolamine. FA triglycerides are typically much less expensive than FA ethyl esters, and the overall process would entail far fewer steps than that described above. As such, the prophetic inventive method is expected to be less expensive, more convenient, and faster than previous methods.

FA triglycerides (6.56 g) can be treated with freshly distilled monoethanolamine (over KOH, 6.53 g, 1:5 mole ratio) and trifluoroacetic acid (10 μL). The mixture can be sealed in an ampul, vigorously shaken, held for 2 h at 140° C., cooled to 25° C., and removed from the ampul. The contents could be treated with $CHCl_3$ (10 mL) and aqueous HCl (10%) until the pH reaches 3. The resulting mixture could be vigorously shaken. The $CHCl_3$ layer could then be separated after layering. The extraction could be repeated twice. The $CHCl_3$ fractions could be combined, dried over anhydrous $Na_2SO_4$, and evaporated in vacuum at 40° C. to constant mass. A yield of 6.67 g (6.54 g for FA triglycerides from flax-seed oil) as an opaque yellowish-orange oil containing 4.86 g (4.78 g for FA triglycerides from flax-seed oil) of FA ethanolamides could be found. The degree of conversion is expected to be about 70%. The purity of the FA ethanolamides can be monitored by TLC. The FA ethanolamides can be purified over a Chemapol L silica-gel column (Kavalier, Czech Rep., 40-100 μm) using a stepped gradient of acetone in hexane (0→10%) calculated as 2 g of starting ethanolamides per 60 g silica gel. A yield 900 mg of purified FA ethanolamides (Rf 0.47) from *saira* fat and flax-seed oil as colorless oily liquids for every 2 g of starting mixture placed on the column could be expected. An analogous procedure could be performed using triglycerides of α-linolenic, eicosapentaenoic, and docosahexaenoic acids to afford FA ethanolamides of these FA (Rf 0.47) as oily liquids in yields of 33, 34, and 35 mg, respectively, for each 100 mg of FA triglycerides used in the reaction. All FA ethanolamides from pure FA triglycerides and from mixtures could be analyzed by HPLC-MS (APCI).

4. Exemplary Prophetic Preparation

One exemplary prophetic preparation could be as follows:
Soft gelatin capsules containing 1 g/per capsule
Composition:
EPA ethanolamide 525 mg/capsule
DHA ethanolamide 315 mg/capsule
Delta-tocotrienol 50 mg/capsule
Gelatine 246 mg/capsule
Glycerol 118 mg/capsule
Red iron oxide 2.27 mg/capsule
Yellow iron oxide 2.27 mg/capsule The active ingredients and the excipients can be weighed and homogenized on a high speed stirrer. The mixture can then be then colloid milled and de-aerated in a stainless steel vessel ready for encapsulation. The mixture can be filled in soft gelatin capsules of size 20 oblong (average weight 1.4 g) using a standard capsulation machine. It is preferred that the delta-tocotrienol be substantially tocopherol-free. The tocotrienol (or TCT) group—together with tocopherols—compose the vitamin E family. Natural tocotrienols exist in four different forms or isomers, named alpha-, beta-, gamma- and delta-tocotrienol, each which contain different number of methyl groups on the chromanol ring. The major structural difference from tocopherol is through its unsaturated side chain that has three double bonds in its farnesyl isoprenoid tail. In the above example, the delta-tocotrienol can be replaced or accompanied with portions of the other three tocotrienols. The above example can be prepared as a medical food, a pharmaceutical preparation, or other variations of preparations that are ingestible by or administrable to a mammal.

5. Standards and Testing for Microbial Contamination of the Oral Solid Dosage Form of the Instant Inventive Composition The publication, "Microbial Bioburden on Oral Solid dosage Forms," by Jose E. Martinez, Pharmaceutical Technology, February 2002, pages 58 to 70, is incorporated herein by reference. For formulations of the instant inventive composition, the water activity is 0.85, testing for TAC and USP indicator organisms is not necessary.

Furthermore, since formulations of the instant inventive composition also have water activity of 0.75, then no detailed microbiological testing of that product should be done.

Total aerobic plate count (TAC) is an estimation of the total viable aerobic bacteria present in a sample of raw material, in-process material, or finished product. Samples are analyzed in accordance with the most current USP Guidelines Chapter <61>, Microbial Limits Test.

Acceptable Total aerobic plate colonies (TAC) for OSDFs are established for the formulations of the inventive composition in terms of alert and action levels, which could be 1000 cfu g/mL and 10,000 cfu g/mL, respectively. A TAC that is 20,000 cfu g/mL is unacceptable.

6. Testing of Formulations of the Instant Inventive Composition

The effects of the prior art formulations of U.S. Pat. No. 5,656,667 (LOVAZA) 4 g per day and of this invention can be assessed in randomized, placebo-controlled, double-blind, parallel-group studies of 84 adult patients (42 on LOVAZA, 42 on placebo) with very high triglyceride levels (Table 2). Patients whose baseline triglyceride levels are between 500 and 2,000 mg/dL can be enrolled in these studies which can have a 6 and 16 weeks' duration. The median triglyceride and LDL-C levels in these patients can be approximately 792 mg/dL and 100 mg/dL, respectively. Median HDL-C level can be about 23.0 mg/dL.

The changes in the major lipoprotein lipid parameters for the groups receiving LOVAZA or the changes expected from the exemplary prophetic formulation above are shown in Table II.

TABLE II

| Parameter | Lovaza Change | Exemplary Formulation Change |
| --- | --- | --- |
| Triglyceride | Decrease 45% | Expected Decrease about 45% |
| LDL-Cholesterol | Increase 45% | Expected Decrease about 20% |

The invention is not limited to the above description. For example, in the exemplary prophetic formulation, delta-tocotrienol is included with the omega-3 fatty acid amides. However, any combination of alpha-, beta-, gamma-, and/or delta tocotrienol may also be included. Further, while amides of DHA and EPA are used in the exemplary prophetic formulation, amides of other omega-3 fatty acids (e.g., selected from the list appearing on Table I above) may be included in addition or in the alternative. While the ethanolamide amides of the omega-3 fatty acids are described, any other amine, whether primary or secondary, aliphatic or aromatic, can be substituted. Additionally, while specific amounts of the amides of DHA and EPA are listed in the exemplary prophetic formulation above, the invention is not so limited; rather, substantially any therapeutically effective amount of these or other amides of omega-3 fatty acids may be incorporated into the formulation.

Also, as mentioned above, the inventive oral formulation may include omega-3 fatty acids and ethanolamine directly instead of omega-3 fatty acid amides (which would metabolize into omega-3 fatty acids and ethanolamine). At least one tocotrienol is preferably included in this formulation.

Moreover, other additives, excipients, and the like may be added or used in the alternative. The actual commercialized product need not be a gelatin-based capsule; "dry" and vegetarian formulations may also be employed. Other variations are also contemplated. For example, the inventive composition should be orally administered in the form of pills, soft capsules or the like. However, the administration could also be through any other route where the active ingredients may be efficiently absorbed and utilized, e.g. intravenously, subcutaneously, rectally, vaginally, or possibly topically.

Having described certain embodiments of the invention, it should be understood that the invention is not limited to the above description. Rather, the scope of the invention is defined by the claims appearing hereinbelow and any equivalents thereof as would be appreciated by one of ordinary skill in the art.

What is claimed is:

1. An orally administered fatty acid composition, for treating high triglycerides and cholesterol in the form of LDL-C comprising:
    an unsaturated Omega-3 Fatty acid amide composition comprising:
    5Z,8Z,11Z,14Z,17Z-eicosapentaenoic ethanolamide (EPA ethanolamide);
    4Z,7Z,10Z,13Z,16Z,19Z-docosahexaenoic ethanolamide (DHA ethanolamide);
    at least one of $\alpha$, $\beta$, $\gamma$ or $\delta$ tocotrienol, wherein said tocotrienol is tocopherol-free; and
    wherein said composition has a total aerobic plate count per g/mL of less than 20,000 cfu.

2. An orally administered fatty acid composition according to claim 1, wherein said EPA ethanolamide is substantially within a range of 100 mg to 900 mg per dosage form.

3. An orally administered fatty acid composition according to claim 1, wherein said DHA ethanolamide is substantially within a range of 100 mg to 900 mg per dosage form.

4. An orally administered fatty acid composition according to claim 1, wherein said at least one tocotrienol is substantially within a range of 10 mg to 500 mg per dosage form.

5. An orally administered fatty acid composition according to claim 1, wherein said at least one tocotrienol includes at least one of $\alpha$-tocotrienol, $\beta$-tocotrienol, $\gamma$-tocotrienol, or $\delta$-tocotrienol.

6. An orally administered fatty acid composition according to claim 1, wherein said composition comprises a pharmaceutical preparation.

7. An orally administered fatty acid composition according to claim 1, wherein said composition comprises a capsule having approximately 525 mg of said EPA ethanolamide, approximately 315 mg of said DHA ethanolamide, and approximately 50 mg of $\delta$-tocotrienol.

8. An orally administered fatty acid composition according to claim 7, wherein said capsule has a gelatin base.

9. An orally administered fatty acid composition according to claim 1, wherein at least one of said EPA ethanolamide or said DHA ethanolamide is synthesized from a respective fatty acid triglyceride.

* * * * *